(12) United States Patent  (10) Patent No.: US 8,038,297 B1
Hofeldt  (45) Date of Patent: Oct. 18, 2011

(54) MULTIFUNCTIONAL GLARE TESTER

(76) Inventor: Albert John Hofeldt, Miami Beach, FL (US)

( * ) Notice: Subject to any disclaimer, the term of this patent is extended or adjusted under 35 U.S.C. 154(b) by 88 days.

(21) Appl. No.: 12/590,118

(22) Filed: Nov. 3, 2009

(51) Int. Cl.
*A61B 3/02* (2006.01)
*A61B 3/00* (2006.01)

(52) U.S. Cl. .................. 351/239; 351/243; 351/246

(58) Field of Classification Search .......... 351/239, 351/200, 237, 246
See application file for complete search history.

(56) References Cited

U.S. PATENT DOCUMENTS

| | | | |
|---|---|---|---|
| 4,784,483 A | 11/1988 | Holliday et al. | |
| 4,800,404 A * | 1/1989 | Ginsburg et al. | 351/243 |
| 5,485,231 A * | 1/1996 | Hayashi et al. | 351/243 |
| 5,537,164 A * | 7/1996 | Smith | 351/219 |
| 5,550,602 A * | 8/1996 | Braeuning | 351/243 |
| 6,027,216 A * | 2/2000 | Guyton et al. | 351/200 |
| 6,783,239 B2 | 8/2004 | Epitropoulos | |
| 6,916,096 B2 * | 7/2005 | Eberl et al. | 351/209 |
| 2010/0091241 A1 * | 4/2010 | Lemay et al. | 351/205 |

* cited by examiner

*Primary Examiner* — Mohammed Hasan

(57) ABSTRACT

A vision-testing device is disclosed that measures glare, macular photostress, and the blue-field entopic phenomenon. Utilizing a mirror, the effective brightness of a small energy efficient light bulb is increased which allows a compact assembly. One embodiment places lights in the line of vision to closely duplicate the glare experience from on coming automobile headlights. The invention provides for testing glare under diffuse and focal lighting conditions which closely mimic environmental lighting conditions.

11 Claims, 6 Drawing Sheets

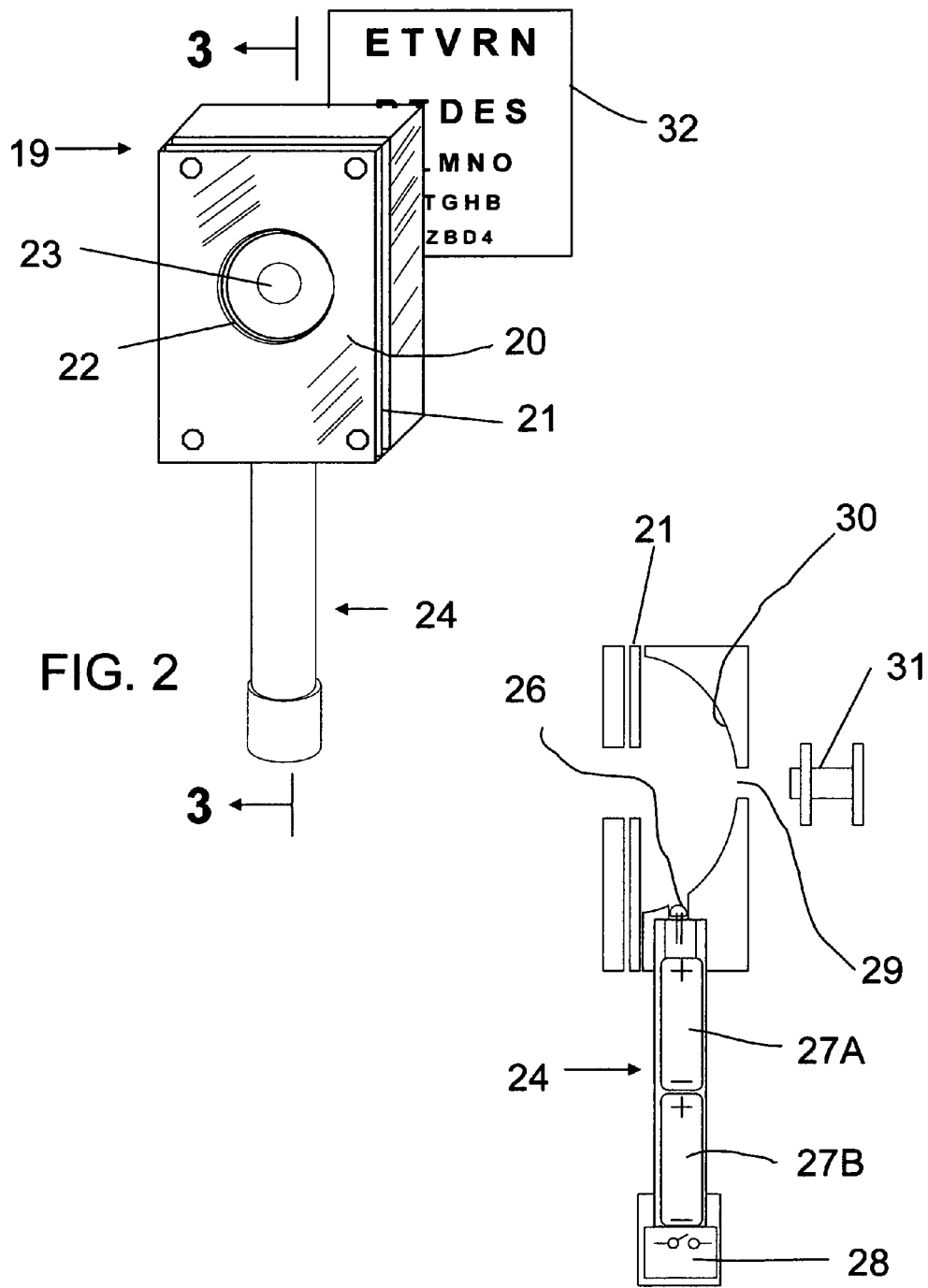

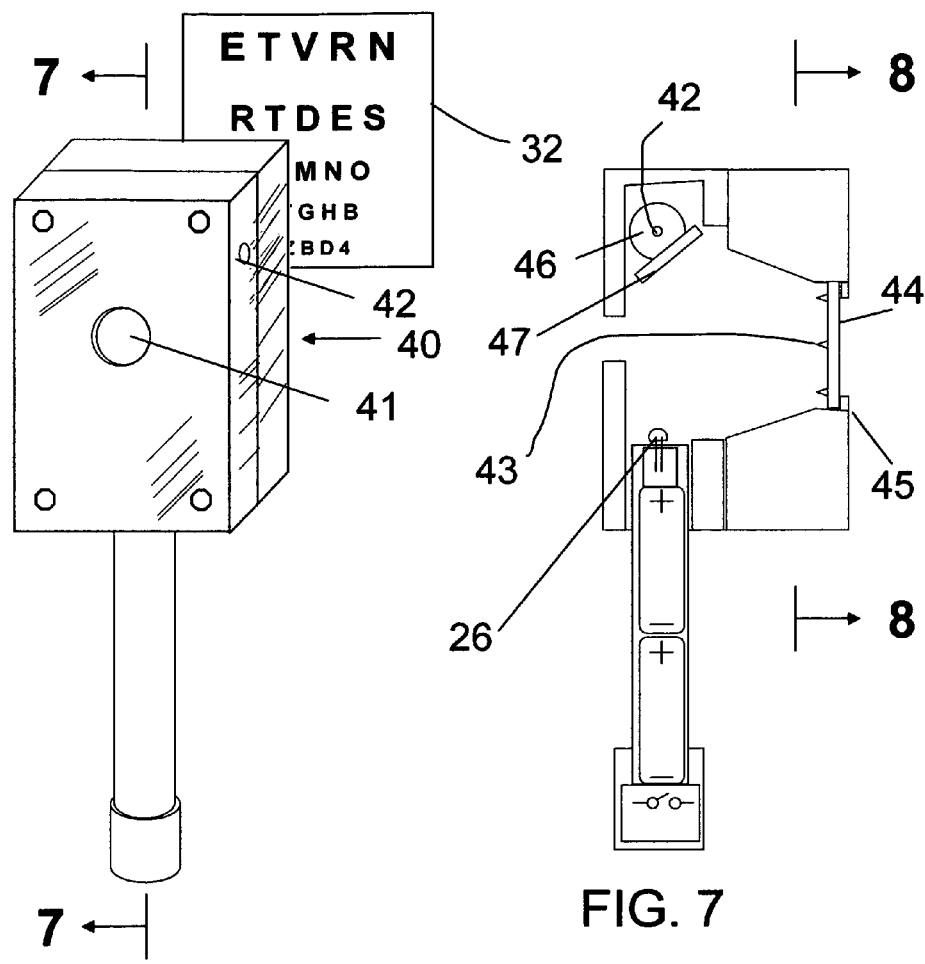
FIG. 6
FIG. 7
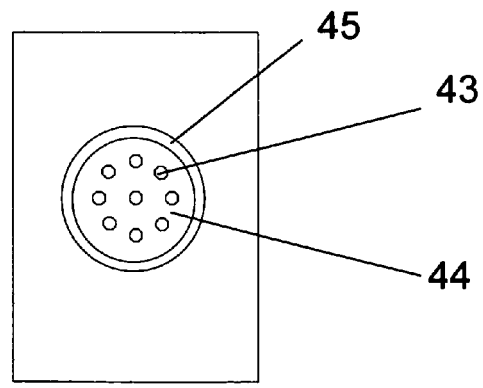
FIG. 8

MULTIFUNCTIONAL GLARE TESTER

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of vision testing and more specifically to a machine for measuring glare in two modes, macular photostress, and blue field entopic phenomenon. Glare testing is well established for evaluating abnormal conditions of the human eye that cause undue scattering of light and visual disability. Disabling glare originates from two lighting modes, diffuse (flood) lighting and focal (spot) lighting. An example of flood lighting is sunlight brightly shining through a picture window and the best example of spot lighting is glaring headlights of oncoming vehicles. Medicare ruling recognizes the impairment and dangers of glare by providing re-imbursements for cataract surgery when visual acuity is less impaired than the visual requirement when glare is not a factor. Glare testing attempts to mimic environmental lighting conditions to demonstrate and document the disability of glare.

The most commonly used glare tester is the flood lighting producing hand-held Brightness Acuity Meter (U.S. Pat. No. 4,784,483). Similar in principle to the Brightness Acuity Meter is the Glare Test Attachment described in U.S. Pat. No. 6,783,239B2, which fits onto an existing illuminating, source, such as, an ophthalmoscope or transilluminator. An example of a spot lighting source glare tester is the AC powered CSV-1OOOHGT (Halogen Glare Test, marketed by Vector Vision, Greenville Ohio) where glare producing spot lights aligning towards the subject are mounted on the sides of the vision chart.

My inventions improves flood lighting producing glare testing by providing a smaller and lower weight instrument for compact assembly without compromising brightness by utilizes a mirrored surface to intensify the light from a low energy LED battery powered light bulb. Another embodiment of my inventions provides for the first time the positioning of glare producing spot lights within the line of sight and this advancement provides testing that closely duplicates approaching automobile headlights, the major environmental glare problem.

Macular photostress testing is a method of detecting diseases of the macular. After saturating the macula of the retina with bright light, there is a period before the function of the macula returns to normal and full vision returns. This refractory period is prolonged in certain diseases of the macula. My invention provides as multifunction device to test photostress and other eye functions The blue-field entopic phenomenon flying corpuscles is elicited by exposing the eye to light in the 425 to 450 nm wavelength range. Under correct conditions of blue light illumination, normal sighted subjects see an entopic phenomenon of tiny light colored darting images in their central field of vision. It is believed that the tiny moving images represent white blood cells circulating through the retinal blood vessels. The absence or a sparsity of this phenomenon is a sign of disease. My invention provides the correct setting for this phenomenon as well as glare testing and photostress testing.

BRIEF SUMMARY OF THE INVENTION

A device for glare testing using two modes of illumination, floods lighting and spot lighting singularly and in combination is described. Utilizing a mirrored surface, the effective brightness of a low energy light bulb is augmented to generate sufficient brightness to provide a compact and low weight tester. The spot lighting mode places the light source, a reflective glittering substance or a miniature light bulb, in the line of vision of the subject and better duplicates the glare from oncoming vehicular headlights than current methods. The flood lighting mode glare tester doubles as a photostress and blue-field entopic phenomenon tester, making the device multifunctional.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 2 is a perspective view of my flood lighting glare tester.

FIG. 3 is a cross sectional view along axis 3-3 of FIG. 2 showing the mirror, the light source, reflective bowl and the plug member for photostress testing.

FIG. 6 is a perspective view of my spot lighting glare tester.

FIG. 7 is a cross-sectional view along axis 7-7 of FIG. 6 showing the light source, the adjustable mirror, the glittering particles on the transparent lens in the rear port.

FIG. 8 is a cross-sectional view along axis 8-8 of FIG. 7 showing the glittering particle of the transparent lens.

REFERENCE NUMERALS IN DRAWINGS

Figure 1A:
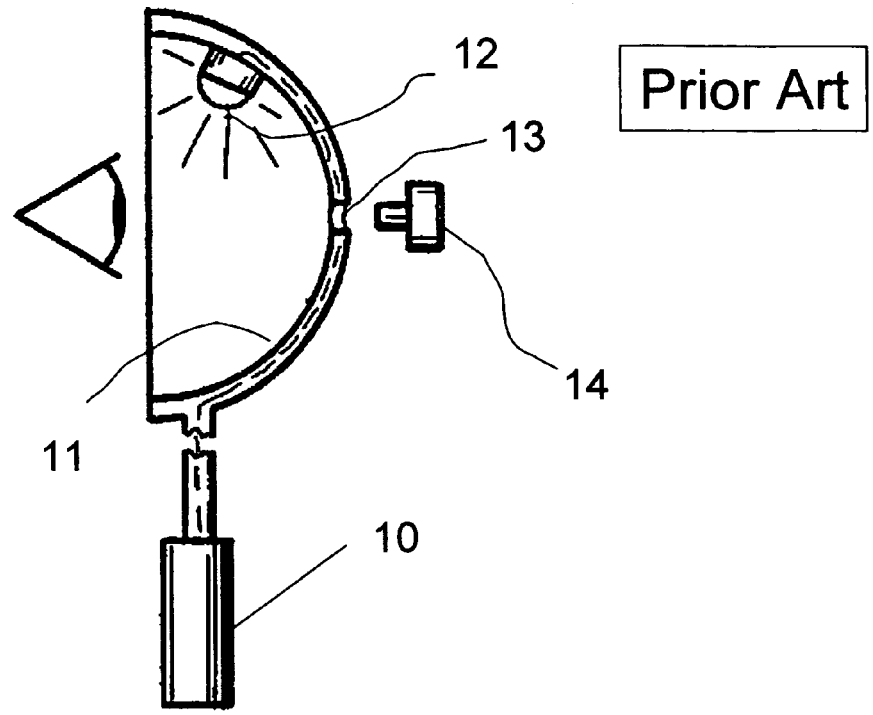
FIG. 1A shows prior art consisting of a cross-sectional view of the Brightness Acuity Meter (U.S. Pat. No. 4,784, 483).

10. Handle
11. Reflective surface
12. Light source
13. Aperture
14. Plug member

15. Glare attachment
16. Removable Plug
17. Support bracket
18. Transilluminator
19. Enclosure
20. Face plate
21. Mirror
22. Front viewing port
23. Rear port
24. Handle
26. Light bulb
27A. Battery
27B. Battery
28. Switch
30. Reflective bowl
31. Plug member
32. Vision chart
33. Lens holder
35. Glittering particles
36. Transparent Lens plug
40. Enclosure
41. Front viewing port
42. Screw for mirror
43. Glittering particles
44. Transparent lens
45. Rim
46. Cylindrical base
47. Mirror
50. Enclosure
51. Front viewing port
52. Miniature electric light bulb
55. Transparent lens
56. Electrical connector
57. Electrical connector
58. Electrical connector
59. Handle
60. Ledge
61. Switch

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriate detailed invention, structure or manner.

Figure 1B:
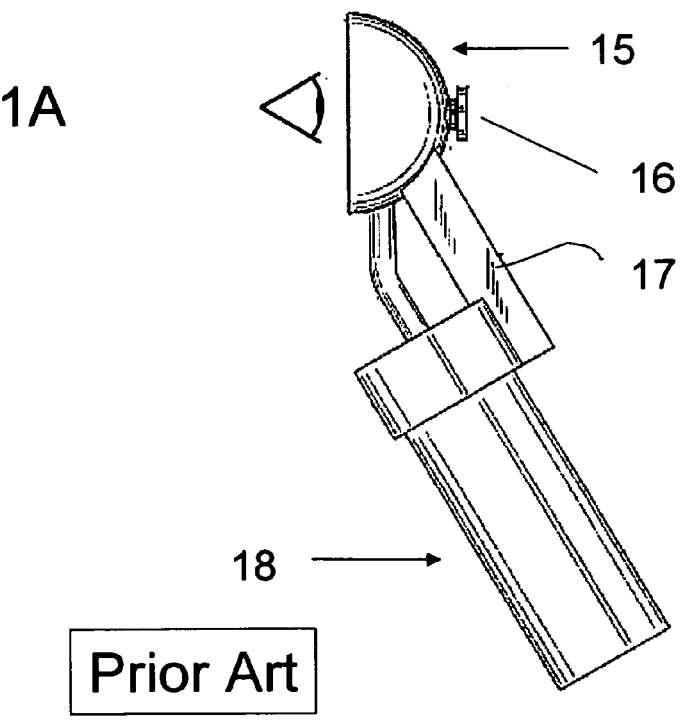
FIG. 1B shows prior art consisting of a perspective view of the Glare Test Attachment (U.S. Pat. No. 6,783,239B2).

FIGS. 1A and 1B are Prior Art. In FIG. 1A is illustrated the BRIGHTNESS ACUITY TESTER, U.S. Pat. No. 4,784,483, showing reflective surface 11 viewed by the eye of the subject, light source 12, aperture 13, plug member 14 for converting glare testing to photostress testing, and handle 10 containing the power supply. In FIG. 1B is illustrated the GLARE TESTER ATTACHMENT, U.S. Pat. No. 6,783,239B2, showing glare attachment 15 having a reflective concave surface viewed by the eye of the subject, removal plug 16 for photostress testing, support bracket 17, and the power and illuminating source, conventional transilluminator 18.

Figure 4:
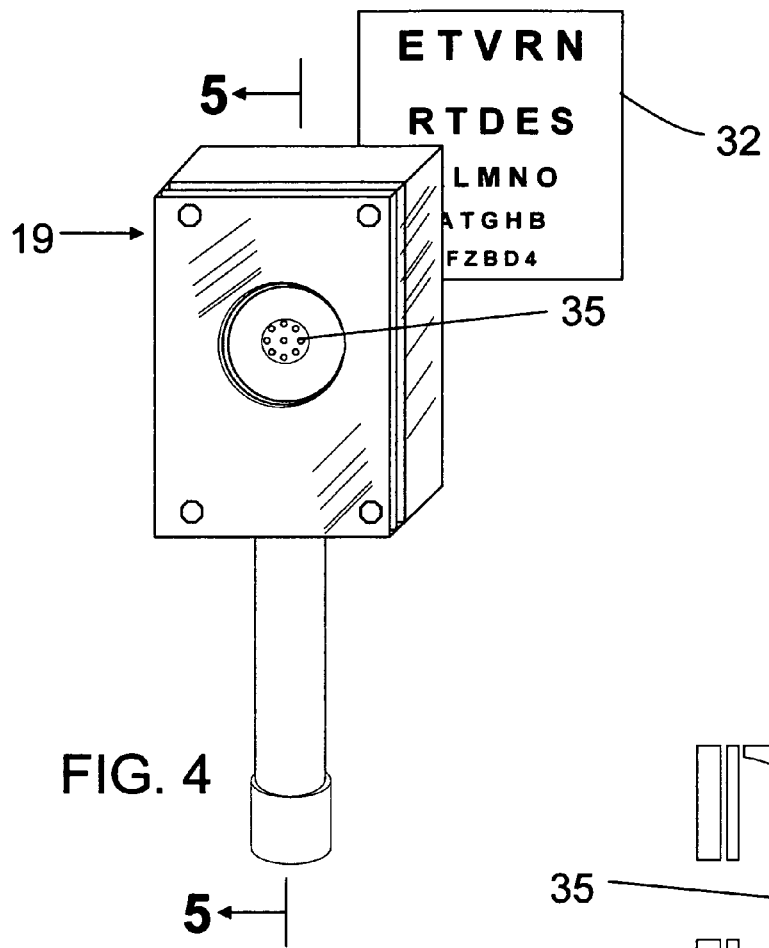
FIG. 4 is a perspective view of my combined flood and spot lighting glare tester with glittering particles on the transparent lens plug seen in the rear port.

Whereas the prior art measure two parameters, glare and photostress, my invention measures three parameters: glare, photostress, and blue-field entopic phenomenon of flying corpuscles. One embodiment of my invention is illustrated in FIGS. 2 and 3 showing enclosure 19 made up of face plate 20, small energy efficient light bulb 26, mirror 21 that redirect light from light bulb 26 onto reflective bowl 30, front viewing port 22, and rear port 23. For glare testing, the subject views vision chart 32 through enclosure 19. Handle 24 contains batteries 27A and 27B and switch 28 having one or more brightness settings that activates light bulb 26 as seen in FIG. 3. Light bulb 26 radiates in the blue portion of the light spectrum which provides stimulus for the blue-field entopic phenomenon when plug member 31 is positioned into rear port 29 while the subject is viewing through front viewing port 22. In conjunction with mirror 21 and reflective bowl 30, light bulb 26 provides sufficient brightness for photostress testing when plug member 31 is positioned into rear port 29 and for flood lightning glare testing when plug member 31 is removed from rear port 29. In FIG. 4 is illustrated another embodiment of my glare tester that combines flood and spot lighting modes by adding a spot lighting source, glittering particles 35, to the glare tester illustrated in FIG. 2. Glittering particles 35 can be composed of diamond, glass, mirror, quartz or other material that produce a radiating reflective light source aimed at the eye of the subject. Transparent lens plug 36 with affixed glittering particles 35 provides the subject an unobstructed view of vision chart 32 and fits into rear port 29. Subjects without abnormal eye conditions see images clearly when sighting through enclosure 19 and transparent lens plug 36 and glittering particles 35 when light bulb 26 is turned on, while subjects with glare producing eye conditions will experience visual impairment commensurate with the disease severity.

Figure 5:
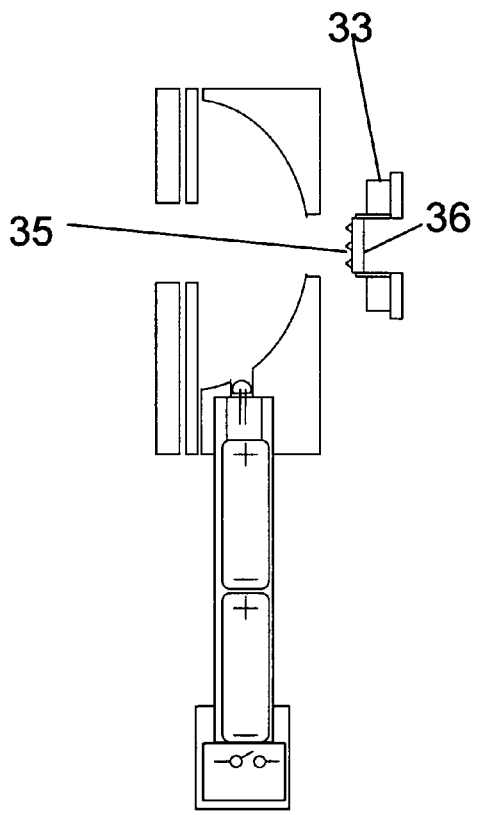
FIG. 5 is a cross sectional view along axis 5-5 of FIG. 4 showing the light source and the removable transparent lens plug with glittering particles.
Figure 9:
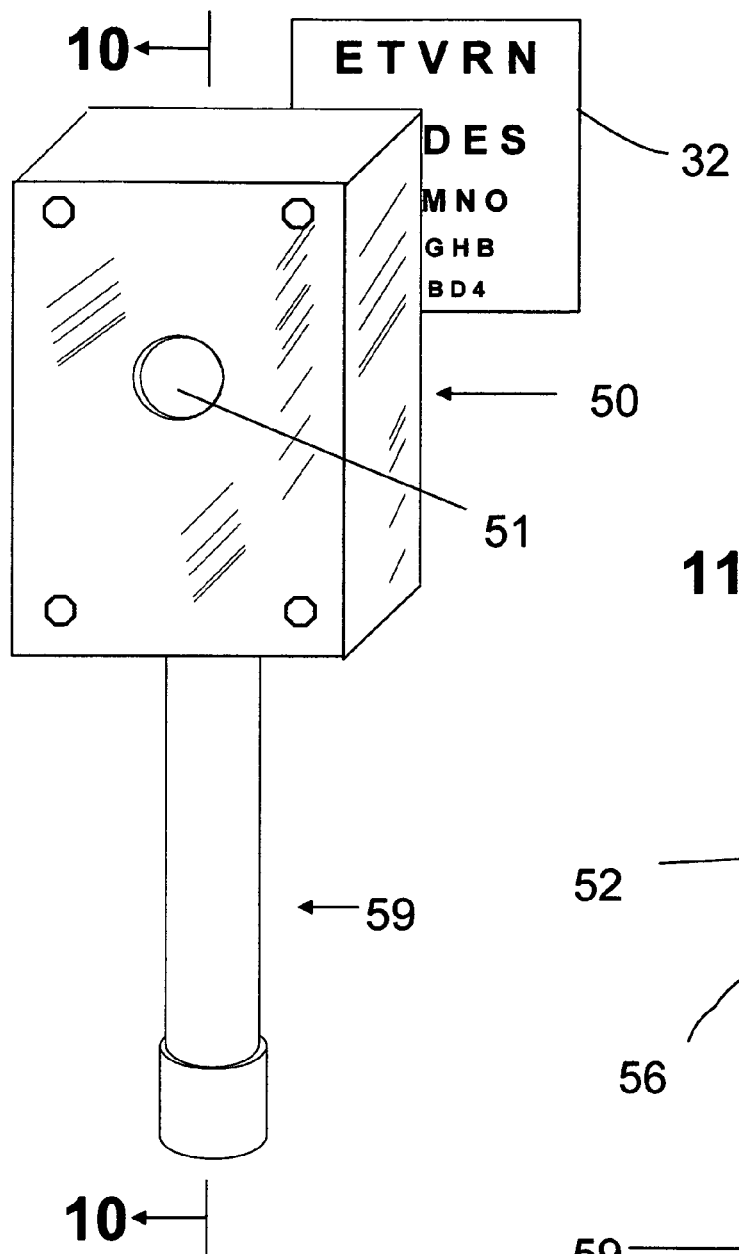
FIG. 9 is a perspective view of my non-reflective glare tester.
Figure 10:
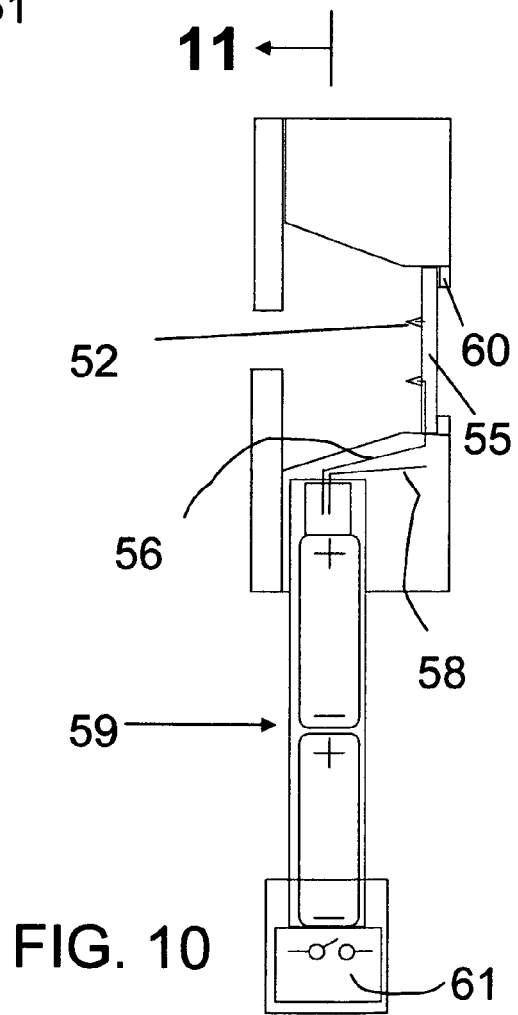
FIG. 10 is a cross-sectional view along axis 10-10 of FIG. 9 showing the miniature electric lights in the rear port.
Figure 11:
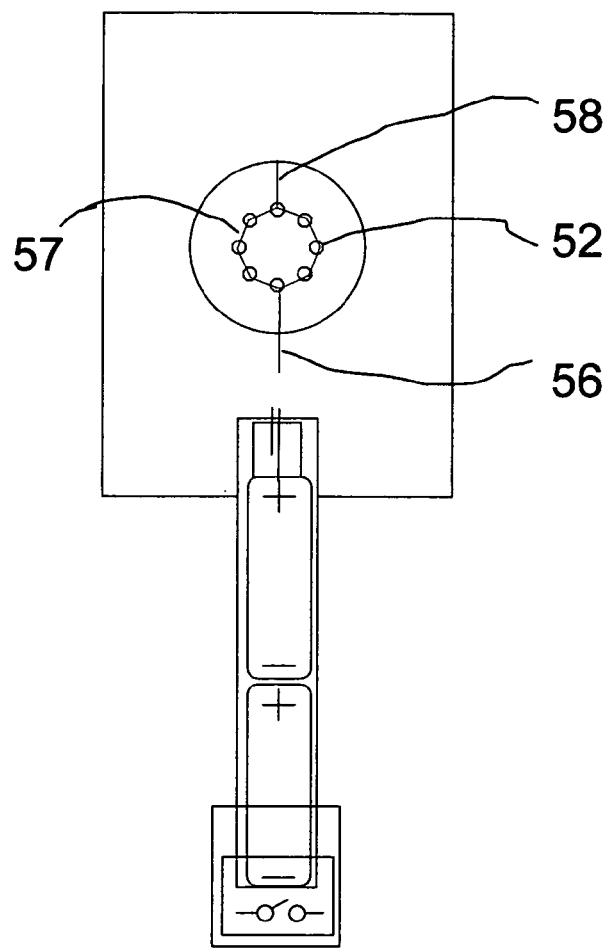
FIG. 11 is a cross-sectional view along axis 11-11 of FIG. 10 showing the ring the miniature lights in the rear port.
Figure 12:
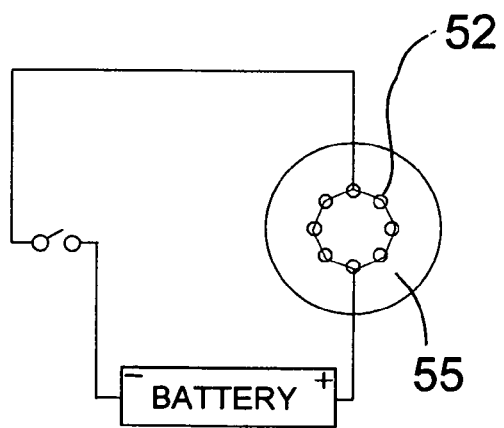
FIG. 12 is diagrammatic view of the circuitry of my non-reflective glare tester.

Turning now to the embodiment of my spot lighting glare tester, FIG. 5 shows enclosure 40 with front viewing port 41 and screw 42 for rotating the alignment of mirror 47 which is mounted on cylindrical base 46 as seen in the cross-section view of FIG. 7. Light radiating from bulb 26 reflects from mirror 47 to illuminate glittering particles 43 on transparent lens 44 affixed to rim 45 as seen in FIGS. 7 and 8.

Another embodiment of my spot lighting glare tester is seen in FIGS. 9-12 which utilizes non-reflective light to test glare. Within enclosure 50 is transparent lens 55 attached to ledge 60 which supports miniature electric light bulbs 52 that are connected through electric connectors 56, 57 and 58 to the power supply housed in handle 59. Switch 61 activates the circuit as diagrammed in FIG. 12 and may have one or several brightness settings. The subject viewing through viewing port 51 has an unobstructed view through the center and periphery of transparent lens 55 while observing eye chart 32. Activating switch 61 produces a spot lighting source within the line of sight that mimics on coming automobile headlights.

What is claimed is:

1. A device for measuring the effect of glare on the human eye comprising:
   a hand-held apparatus housing a light source that radiates white appearing light containing a predominance of 430 nm wavelength light onto a concave reflective bowl and a mirror with said mirror redirecting the light onto said reflective bowl which is aligned to reflect light into the eye of the subject with said bowl having a central opening for viewing a visual target,
   whereby, the light reflected by the mirror onto the reflective bowl intensifies the light incident to the eye of the subject.

2. A device as in claim 1 where the device is battery powered and has a switch with one or more intensity settings.

3. A device as in claim 1 that is multifunctional when a plug is positioned within said central opening to reflect the maximum amount of light into the eye of the subject to photostress the retina.

4. A device as in claim 1 that is multifunctional having said light source emitting light in the blue portion of the light spectrum and said plug is positioned into said central opening to reflect light into the eye of the subject for observing the entopic phenomenon of flying corpuscle movement.

5. A device as in claim 1 that is multifunctional having said light source emitting light in the blue portion of the light spectrum and said plug is positioned into said central opening to reflect light into the eye of the subject for observing the entopic phenomenon of flying corpuscle and to photostress the retina.

6. A device as in claim 1 where a transparent lens having associated reflective material affixed is positioned within said central opening with said reflective material arranged so that the view through said transparent lens is not obstructed and said discrete points are capable of producing glare in a subject prone to glare, whereby, the device combines flood and spot lighting to measure glare.

7. A device for measuring the effect of glare on the human eye comprising:
   (a) an enclosure having a proximal aperture and a distal aperture with said proximal aperture facing the human subject and said distal aperture facing the viewing target, with said enclosure housing a transparent structure within the line of sight of said subject and positioned between said proximal and distal apertures,
   (b) a base affixed to said enclosure with said base housing a power source, a light source, switch, and brightness controls, and
   (c) one or more minute mirrors mounted onto the surface of said transparent structure within but not blocking the line of sight of said subject, with said minute mirrors reflecting light from said light source into the line of sight of said subject which produces glare in a subject prone to glare.

8. A device as in claim 7 that where said discrete point of light is a reflective substance that is illuminated by a light source.

9. A device as in claim 7 where said base is a handle that fits into a human hand.

10. A device for measuring the effect of glare on the human eye comprising:
    (a) an enclosure having a proximal aperture and a distal aperture with said proximal aperture facing the human subject and said distal aperture facing the viewing target, with said enclosure housing a transparent structure within the line of sight of said subject and positioned between proximal and distal apertures,
    (b) a base affixed to said enclosure that with said base housing a power source, a light source, switch, and brightness controls, and
    (c) one or more light emitting sources connected by circuitry to said power source with said light emitting sources mounted on said transparent structure within the line of sight of said subject, and capable of produces glare in a subject prone to glare.

11. A device as in claims 10 where said base is a handle that fits into a human hand.

\* \* \* \* \*